(12) United States Patent
Thompson (10) Patent No.: US 7,313,529 B2
(45) Date of Patent: Dec. 25, 2007

(54) PORTABLE EXTENDER FOR DATA TRANSMISSION WITHIN A MEDICAL DEVICE COMMUNICATION SYSTEM

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1245 days.

(21) Appl. No.: 09/887,762

(22) Filed: Jun. 22, 2001

(65) Prior Publication Data

US 2002/0077841 A1 Jun. 20, 2002

Related U.S. Application Data

(60) Provisional application No. 60/213,858, filed on Jun. 23, 2000.

(51) Int. Cl.
*G06F 19/00* (2006.01)

(52) U.S. Cl. .............. 705/3; 607/30; 607/32; 607/60; 600/300; 600/513; 370/338; 128/903

(58) Field of Classification Search ............ 705/2, 705/3, 4, 8, 9; 607/30, 32, 60; 600/300, 600/513; 370/33; 128/903
See application file for complete search history.

(56) References Cited

U.S. PATENT DOCUMENTS

| | | | | |
|---|---|---|---|---|
| 4,476,868 A | | 10/1984 | Thompson | 128/419 PG |
| 4,809,697 A | * | 3/1989 | Causey et al. | 607/31 |
| 5,052,388 A | | 10/1991 | Sivula et al. | 128/419 PG |
| 5,235,702 A | * | 8/1993 | Miller | 707/102 |

(Continued)

FOREIGN PATENT DOCUMENTS

GB  2341103  8/1999

OTHER PUBLICATIONS

Schoenfeld, Mark H., Pacemaker Programmers: An Updated Synopsis, Cardiac Electrophysiology Review; Jul. 1999, p. 20.*

*Primary Examiner*—Jeffrey A. Smith
*Assistant Examiner*—R. David Rines
(74) *Attorney, Agent, or Firm*—Michael C. Soldner (57) ABSTRACT

Apparatus and method for managing chronic home care of patients with one or more implanted medical devices (IMDs) includes a mobile portable device for use by a visiting nurse. Specifically, the portable device integrates various systems to enable the nurse to schedule her day and get directions to a first and subsequent visit destination via a GPS system or equivalent. The portable device includes an identification system including a security protocol to identify the nurse/home health care provider. Additionally, the portable device incorporates a communication system such as a cellular phone that would enable the nurse to connect to other clinical support personnel such as a doctor or a specialist. The portable device further includes a wireless communication system that enables communication between the portable device and one or more IMDs in a patient. Upon arrival at the patient's home, the nurse may download data from the one or more IMDs directly into the portable device. This data could in turn be downloaded immediately or later to a remote viewing center via conventional data transmission systems. Other medical data such as blood pressure measurements and vital physiologic signals may be entered into the portable device using a digitizer pen, voice input or equivalent. Similar to the IMD data, this medical data could be transmitted to the remote location from the portable device.

9 Claims, 5 Drawing Sheets

U.S. PATENT DOCUMENTS

| | | | |
|---|---|---|---|
| 5,456,692 A | 10/1995 | Smith, Jr. et al. | |
| 5,544,649 A * | 8/1996 | David et al. | 600/301 |
| 5,553,609 A | 9/1996 | Chen et al. | 128/630 |
| 5,749,908 A | 5/1998 | Snell | 607/30 |
| 5,752,976 A | 5/1998 | Duffin et al. | 607/32 |
| 5,756,941 A | 5/1998 | Snell | 178/18 |
| 5,787,186 A | 7/1998 | Schroeder | 382/115 |
| 5,792,204 A | 8/1998 | Snell | |
| 5,833,623 A | 11/1998 | Mann et al. | |
| 5,841,971 A * | 11/1998 | Longginou et al. | 709/200 |
| 5,843,139 A | 12/1998 | Goedeke et al. | 607/32 |
| 5,872,923 A | 2/1999 | Schwartz et al. | 395/200.35 |
| 5,924,074 A * | 7/1999 | Evans | 705/3 |
| 5,948,040 A * | 9/1999 | DeLorme et al. | 701/201 |
| 5,991,429 A * | 11/1999 | Coffin et al. | 382/118 |
| 6,016,476 A | 1/2000 | Maes et al. | 705/1 |
| 6,177,905 B1 | 1/2001 | Welch | 342/357.13 |
| 6,307,956 B1 * | 10/2001 | Black | 382/124 |
| 6,327,501 B1 * | 12/2001 | Levine et al. | 607/27 |
| 6,331,160 B1 * | 12/2001 | Bardy | 600/300 |
| 6,411,899 B2 * | 6/2002 | Dussell et al. | 701/211 |
| 6,463,417 B1 * | 10/2002 | Schoenberg | 705/2 |
| 6,553,262 B1 * | 4/2003 | Lang et al. | 607/32 |
| 6,591,242 B1 * | 7/2003 | Karp et al. | 705/2 |
| 6,597,392 B1 * | 7/2003 | Jenkins et al. | 348/207.1 |
| 2002/0016568 A1 * | 2/2002 | Lebel et al. | 604/131 |

* cited by examiner

PORTABLE EXTENDER FOR DATA TRANSMISSION WITHIN A MEDICAL DEVICE COMMUNICATION SYSTEM

RELATED APPLICATIONS

This application claims priority to provisionally-filed patent application Ser. No. 60/213,858 filed Jun. 23, 2000, and which is incorporated herein by reference in its entirety.

FIELD OF THE INVENTION

The present invention generally relates to medical devices and communications systems. Specifically, the invention relates to a portable extender that is in wireless communication with a device implanted in a patient. The extender is a computer that transmits and exchanges data between a patient station and a remote expert station. The patient station and remote expert station maintain data communication via network systems such as the Internet, worldwide web, intranet, extranet, or other similar network systems.

BACKGROUND OF THE INVENTION

The concept of home health care began in the 1850's when traveling health care professionals, usually physicians, provided in-home visits to patients who were in need of health care and were unable to seek such care outside of the home. From the outset, however, traveling between various patients' homes constituted "downtime" for the health care professional. In the middle of the twentieth century, this type of medical service was transferred from the physician to nurses or other health care workers. During the past decade, providing home health care has become more difficult due to the shortage of health care professionals in general and, in particular, of those who provide home health care. Because of this shortage as well as the increase in medical costs, home health care visits may be limited to basic needs and/or medical emergencies.

On the other hand, the number of patients who are home bound has been increasing. Many terminally ill patients, such as heart failure or cancer patients among others, are sent home to live with their families who provide 24-hour care. Other patients with chronic health problems reside in their homes where they receive necessary support and treatment on an "as needed" basis. Through the auspices of hospices or other support groups, nurses or health care workers provide medical care and evaluation on a periodic basis. Although these visits provide the contracted services, nonetheless they still suffer from administrative "overload" tasks.

The nurse or other health care worker may spend much of her time on the phone, contacting physicians, druggists, plan administrators, the family members of the patient, and so on. In addition, that same nurse must take notes and/or fill out health plan or HICFA forms to ensure reimbursement for the services provided. As a result, a large percentage of the time during the visit has little to do with providing medical care and evaluation of the patient.

Patients with implantable medical devices (IMDs) also require regular checkups to determine whether their IMDs have been functioning properly. Most patients with IMDs must be monitored bi-annually, at the very least. Such monitoring may occur transtelephonically from the patient's home or via telemetry as has been disclosed in U.S. Pat. No. 5,752,976 issued to Duffin, et al, "World Wide Patient Location and Data Telemetry System for Implantable Medical Devices", incorporated herein by reference in its totality. Still, some of the very elderly patients with IMDs, whether single or multiple, require periodic visits from health care nurses/workers to evaluate their IMD(s).

Various solutions to these issues, in addition to the '976 patent, have been suggested in the art. U.S. Pat. No. 5,553,609 issued to Chen, et al, "Intelligent Remote Visual Monitoring System for Home Health Care Service" generally discloses a computer-based remote visual monitoring system connected transtelephonically to a remote master-monitoring computer. This system is intended for use by the visiting nurse during an in-home patient health care visit. Separate audio and visual equipment facilitates communication between the patient's home and a remote station. The system has several layers, including units in the patient's home, the caregiver's office, and the supervisory control center. Audiovisual equipment in the patient's home and at the caregiver's office provides two-way communications during a home visit. There is also a provision for generating and maintaining the patient's medical records. The '609 patent, however, does not appear to teach a method for monitoring patients with IMDs. U.S. Pat. No. 5,749,908 issued to Snell, "Methods and Apparatus for Annotating Data in an Implantable Device Programmer Using Digitally Recorded Sound", teaches a system in which data from an IMD patient may be downloaded to a programmer using digitally recorded voice signals and/or digitizer pen. A physician, upon reviewing the data, can listen to the voice annotations by using a playback mode. While the '908 patent addresses issues that are specific to patients with IMDs, it implements the use of a device programmer. Further, desirable features such as a method to address or deal with the previously cited administrative tasks, that consume so much time during a typical visit, appear to be undisclosed by the '908 patent.

U.S. Pat. No. 5,872,923 issued to Schwartz, et al, "Collaborative Video Conferencing System" discloses a video conferencing system, wherein multiple parties at different locations can view, and modify, a common image on their computer displays. The invention also provides a video camera at each computer, which takes a video picture of each party. The systems described in the '609 and '923 patents, however, appear to depend on static, non-mobile computer terminals.

What is needed to optimize the tasks for the home health care worker is a mobile device akin to a Personal Data Assistant (PDA) disclosed in U.S. Pat. No. 6,016,476, issued to Maes, et al, "Portable Information and Transaction Processing System and Method Utilizing Biometric Authorization and Digital Certificate Security" incorporated herein by reference in its totality. The PDA in this patent is a portable device with a touch screen, with a microphone and local CPU for processing voice commands and user verification. While the '476 patent is intended for managing financial data, its general concept may underlie certain aspects of the present invention. One aspect of particular interest, for example, is a method to verify the identity of the user via voice recognition. An alternative method for identifying the user is disclosed in U.S. Pat. No. 5,787,186 issued to Schroeder "Biometric Security Process for Authenticating Identity and Credit Cards, Visas, Passports and Facial Recognition" in which a person's facial structure is used to verify a person's identity. The '186 patent teaches the use of an image capturer such as a scanner or a video camera to capture facial features that are transferred to the CPI for an analysis of a basic facial image. If matched to the stored image, the user can gain entry into files containing secure data.

Inputting data may be accomplished via a digitizer pen, tethered to a PDA, as disclosed in U.S. Pat. No. 5,756,941, issued to Snell "Retractable Pen Tether for a Digitizer Pen and Method of Attaching a Digitizer Pen to a Digitizer", incorporated herein by reference in its totality. Such a pen is intended for use in a hand-held computer and is kept in a pen storage chamber incorporated within the body of the PDA. Such digitizer pens, though not tethered to the PDA as taught by the '941 patent, are now commonly available with commercial PDAs. Such common use should make these digitizer pens an easy-to-use tool for the home health care worker.

A health care worker must often spend a good deal of time trying to determine where she must go for her next visit, especially if the next visit is a new patient. U.S. Pat. No. 6,177,905 issued to Welch "Location-Triggered reminder for Mobile User Devices", discloses how to equip a PDA with a global positioning system (GPS) receiver. The user can program into the PDA geographical coordinates of locations and, thereafter, give them names. These names can then be called up and, by reference to one's present location, provide directions to a new location which, in this context, could be the next visit.

What is needed is a system that provides all the benefits of home health care service with methods and structures implemented to enable monitoring of IMD patients on a regular basis.

SUMMARY OF THE INVENTION

In one aspect of the present invention a visiting nurse is enabled to schedule her day and get directions to the first and subsequent visits via a GPS or equivalent tool. Upon arriving at the patient's home, she can download data from the IMD directly into a mobile portable extender device. In yet another aspect of the invention, data from the extender could be downloaded immediately or later to a remote viewing center.

Yet another feature enables the nurse to ask questions by initiating voice and/or video communication with a physician via the audio and video capabilities of the portable extender device. Further, the nurse can call such an expert to discuss patient treatment or other clinical procedures. Other medical data such as blood pressure (BP) measurements from those gathered via a BP cuff can be entered via a digitizer pen or voice input. Furthermore, the nurse may automatically change a prescription by contacting a druggist electronically. All these actions are accomplished via a cellular connection that allows voice, video, and text communication with remote facilities. Documentation may be required, such as a Medicare 485 form that documents the actions taken during a visit. This form can be downloaded to the portable extender and automatically filled out. Thus, many time-consuming data management tasks are centralized in and by the portable extender device.

All of these capabilities are available to the nurse in the present invention. The nurse need not make multiple phone calls to contact different people, nor rewrite the prescription back at the office and then send it out to the patient or the pharmacy.

Thus, monitoring of the patient in the home is expedited. Shorter, more focused visits would allow the nurse to visit approximately 50% more patients in a day. In one embodiment, the portable extender contains a microphone as well as a video camera similar to the video cam found in many PCs. Contact with remote location occurs via a cellular phone or equivalent communication device contained in the portable extender. The portable extender could be easily assembled with off-the-shelf materials or may implement proprietary software loaded into a commercially available device such as the Fujitsu Stylistic 1200™ Pen Tablet.

DETAILED DESCRIPTION OF THE DRAWINGS

Figure 1:
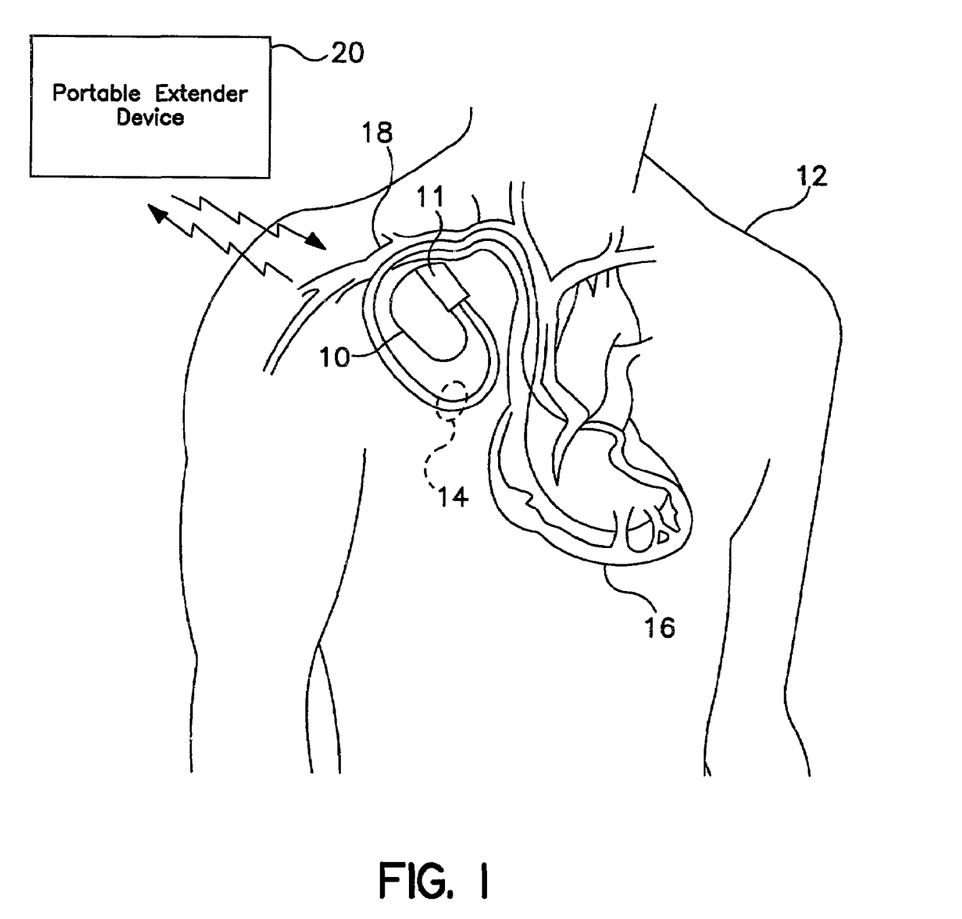
FIG. 1 is an illustration of a body-implantable device system in accordance with the present invention, including a hermetically sealed device implanted in a patient and an external transceiver.

FIG. 1 is an illustration of an implantable medical device system adapted for use in accordance with the present invention. The medical device system shown in FIG. 1 includes implantable device 10—a pacemaker for illustration purposes—that has been implanted in patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

The present invention will be described herein in an embodiment that includes a pacemaker. Those of ordinary skill in the art, however, with the benefit of the present disclosure will appreciate that the present invention may be practiced in connection with numerous other types of IMDs such as defibrillators, cardioverters, neurostimulators, insertable loop recorders (ILR) such as the Medtronic® Reveal™, heart failure monitors such as the Medtronic® Chronicle™, and the like. Indeed, the present invention may be practiced in any application in which it is desirable to provide a communication link between two physically separated components. Also depicted in FIG. 1 is a portable extender unit 20 for non-invasive, wireless communication with implanted device 10 via uplink and downlink communication channels, to be hereinafter described in further detail.

Figure 2:
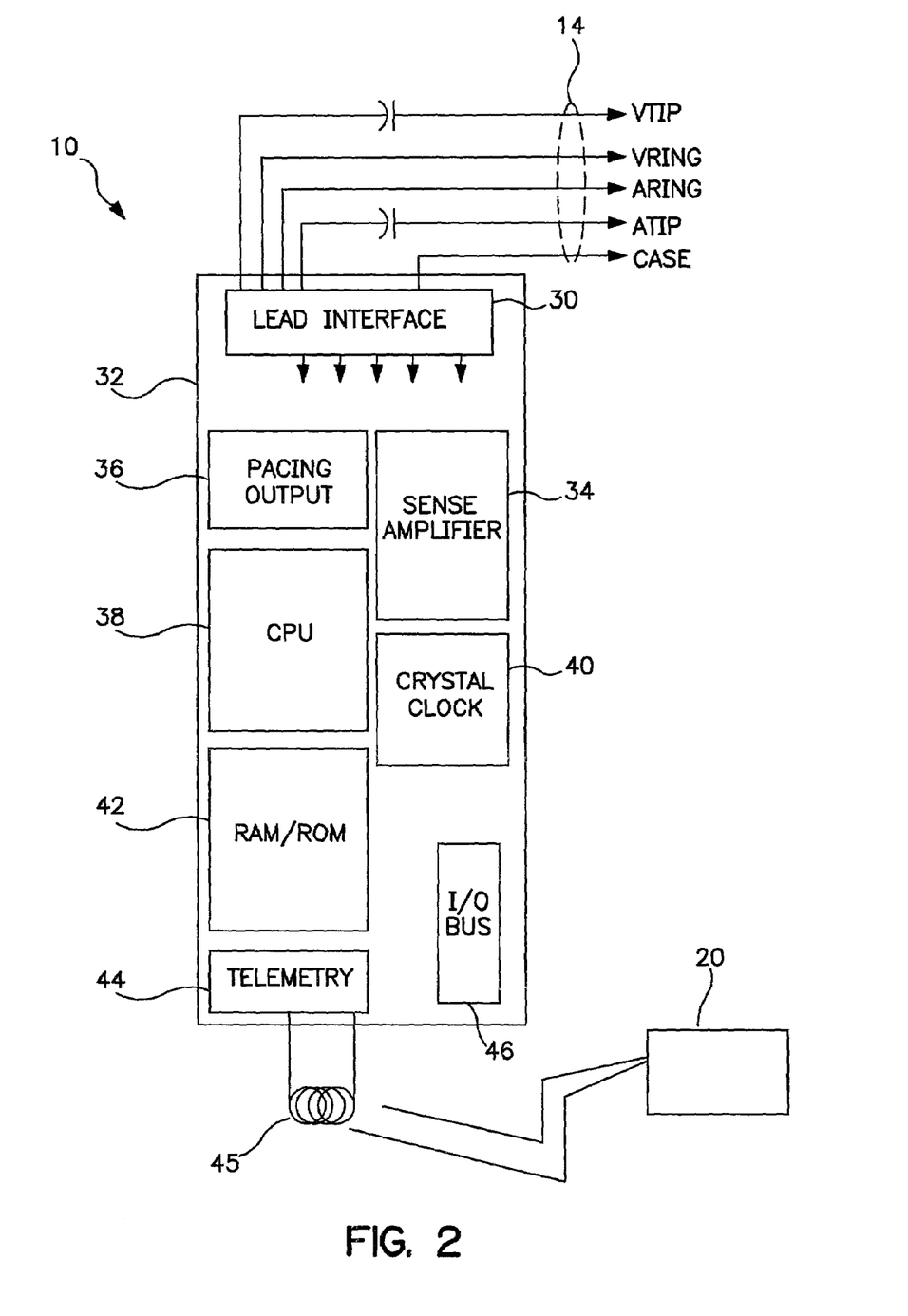
FIG. 2 is a block diagram of the implanted device from FIG. 1.

FIG. 2 is a block diagram of the electronic circuitry that makes up pulse generator 10 in accordance with the presently disclosed invention. As can be seen from FIG. 2, pacemaker 10 comprises a primary stimulation control circuit 32 for controlling the device's pacing and sensing functions. The circuitry associated with stimulation control circuit 32 may be of conventional design, in accordance, for example, with what is disclosed U.S. Pat. No. 5,052,388 issued to Sivula et al., "Method And Apparatus For Implementing Activity Sensing In A Pulse Generator". To the extent that certain components of pulse generator 10 are conventional in their design and operation, such components will not be described herein in detail, as it is believed that design and implementation of such components would be a matter of routine to those of ordinary skill in the art. For example, stimulation control circuit 32 in FIG. 2 includes sense amplifier circuitry 34, stimulating pulse output circuitry 36, a crystal clock 40, a random-access memory and read-only memory (RAM/ROM) unit 42, and a central processing unit (CPU) 38, all of which are well-known in the art. Pacemaker 10 also includes internal communication circuit 44 so that it is capable of wirelessly communicating with portable extender device 20.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 30 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 34 and stimulating pulse output circuit 36, in accordance with common practice, such that cardiac electrical signals may be conveyed to sensing circuitry 34, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 32 includes central processing unit 38 which may be an off-the-shelf programmable microprocessor or micro controller, but in the present invention is a custom integrated circuit. Although specific connections between CPU 38 and other components of stimulation control circuit 36 are not shown in FIG. 2, it will be apparent to those of ordinary skill in the art that CPU 38 functions to control the timed operation of stimulating pulse output circuit 36 and sense amplifier circuit 34 under control of programming stored in RAM/ROM unit 42. It is believed that those of ordinary skill in the art will be familiar with such an operative arrangement.

With continued reference to FIG. 2, crystal oscillator circuit 40, in the presently preferred embodiment a 32,768-Hz crystal controlled oscillator provides main timing clock signals to stimulation control circuit 32. Again, the lines over which such clocking signals are provided to the various timed components of pulse generator 10 (e.g., microprocessor 38) are omitted from FIG. 2 for the sake of clarity.

It is to be understood that the various components of pulse generator 10 depicted in FIG. 2 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 36, which functions to generate cardiac stimuli under control of signals issued by CPU 38, may be, for example, of the type disclosed in U.S. Pat. No. 4,476,868 to Thompson, entitled "Body Stimulator Output Circuit", which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 34, which is of conventional design, functions to receive electrical cardiac signals from leads 14 and to process such signals to derive event signals reflecting the occurrence of specific cardiac electrical events, including atrial contractions (P-waves) and ventricular contractions (R-waves). Sense amplifier circuit 34 provides these event-indicating signals to CPU 38 for use in controlling the synchronous stimulating operations of pulse generator 10 in accordance with common practice in the art. In addition, these event-indicating signals may be communicated, via uplink transmission, to portable extender device 20 via telemetry coil 45. Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 44 in pacemaker 10, and an associated communication subsystem in portable extender device 20.

Figure 3A:
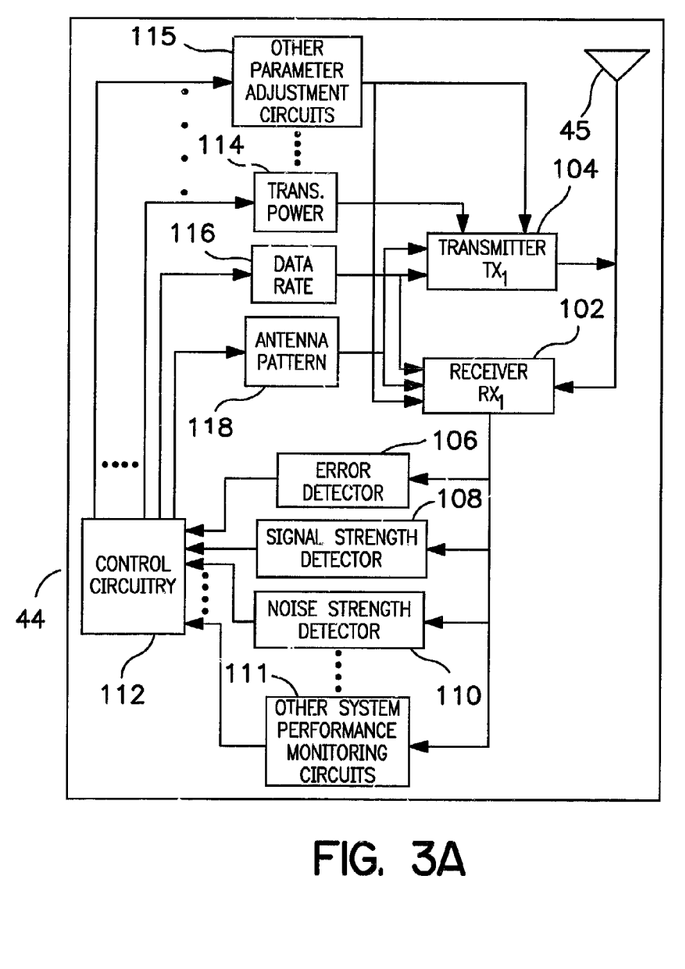
FIG. 3a is a block diagram showing the communication system in accordance with the present invention from the implanted device of FIG. 2.

Referring to FIG. 3*a*, there is shown a simplified block diagram of communication subsystem 44 from pacemaker 10, in accordance with the present invention. Communications subsystem may be, for example, of the type disclosed in U.S. Pat. No. 5,843,139 to Goedeke, et al., "Adaptive Performance-Optimizing Communication System for Communicating With an Implanted Medical Device", which patent is incorporated by reference herein in its entirety.

Communication subsystem 44 in implantable device 10 includes a receiver 102 and a transmitter 104 each coupled to antenna 45 (FIG. 2) which may be implemented as a multiple-turn wire coil, a stub wire, or a pacing lead. In one embodiment, communication subsystem 44 further includes error detection circuitry 106, signal strength detection circuitry 108, and noise strength detection circuitry 110. Generally, error detection circuit 106, signal strength detection circuit 108, and noise strength detection circuit 110, can be called system performance monitoring circuits which function to dynamically monitor one or more aspects of communication system 44. Error detection circuit 106, for example, may utilize well-known error detection techniques to determine the bit error rate (BER) and the SNR of digital information received by receiver 102. Signal strength detector circuit 108 may consist of a logarithmic amplifier that detects and filters the RF signal (or IF signal if downconverted) to provide an RSSI (received signal strength indicator) output that gives a voltage proportional to the logarithm of the signal strength at the receiver's RF input. Detector 108 will only respond to the signal present within the receiver pass band. In this way, the desired signal strength (actually, signal plus noise) can be measured. Likewise, the noise can be measured with the same apparatus under the condition of a known period with no received transmission. In this way the signal-to-noise ratio of the received signal can be measured by a simple comparison of the signal and the noise RSSI samples. This method, as would be appreciated by those of ordinary skill in the art, would effectively implement circuit 110 as well as 108 in FIG. 3.

Figure 4:
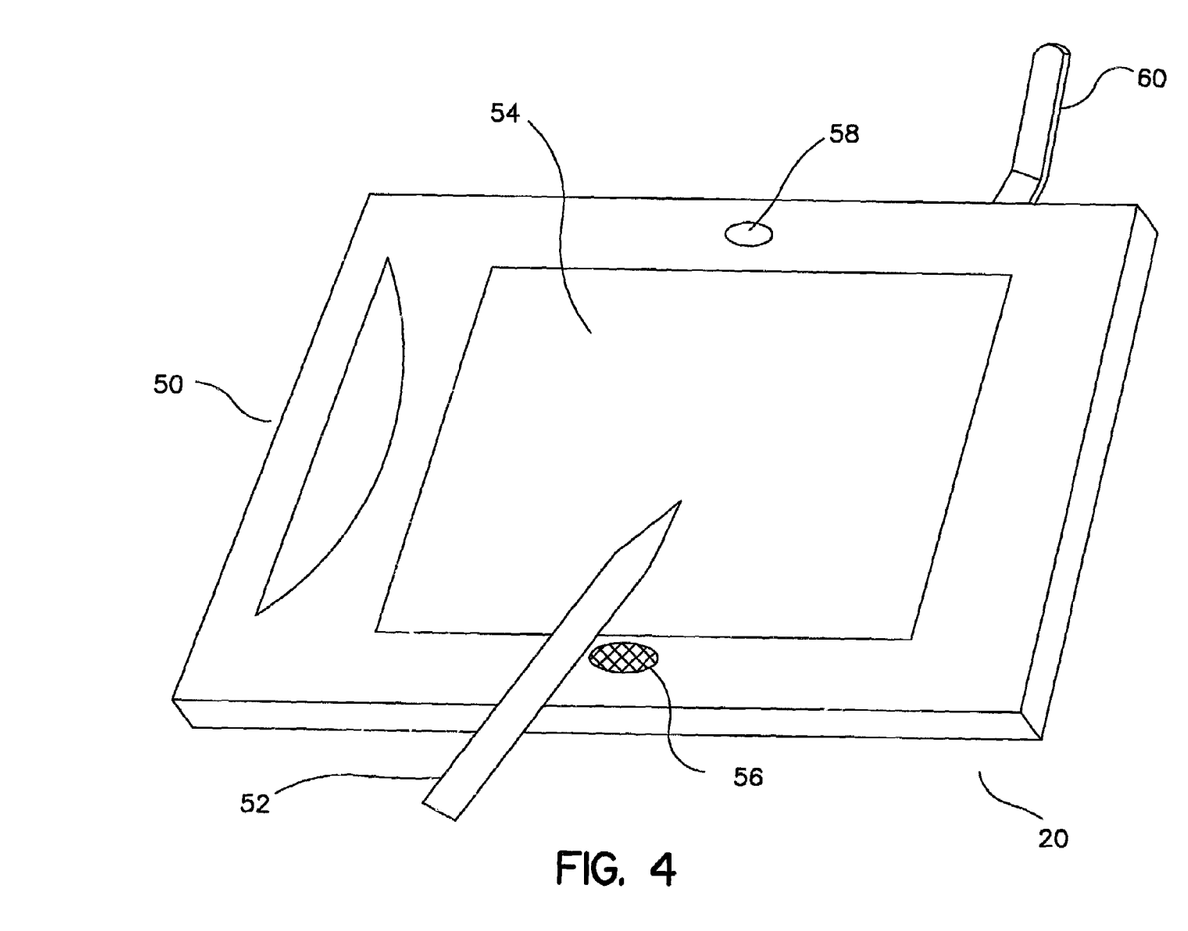
FIG. 4 is an illustration of one embodiment of the portable extender device.

With continued reference to FIG. 3a, circuits 106, 108 and 110 are in turn coupled to control circuit 112 that, in one embodiment, may be a custom integrated circuit or equivalent. Control circuit 112 in communication subsystem 44 functions to control various aspects of communication operation in device 10, and further functions to cause data to be transmitted to portable extender device 20 (FIG. 4). For example, as shown in FIG. 3a, control circuit 112 is coupled to transmitter power control circuit 114, such that under command of control circuit 112, the power of signals transmitted by transmitter 104 can be adjusted up or down. Similarly, control circuit 112 is coupled to data rate control circuit 116 that controls the rate at which data is transmitted from transmitter 104. Control circuit 112 is also coupled to an antenna pattern (field strength as a function of position) control circuit 118, so that the antenna pattern for reception and transmission of transmitted signals may be dynamically configured during operation of communication subsystem 44 and to receiver circuit 102 so that the bandwidth of the bandpass filter therein may be adjusted.

Figure 3B:
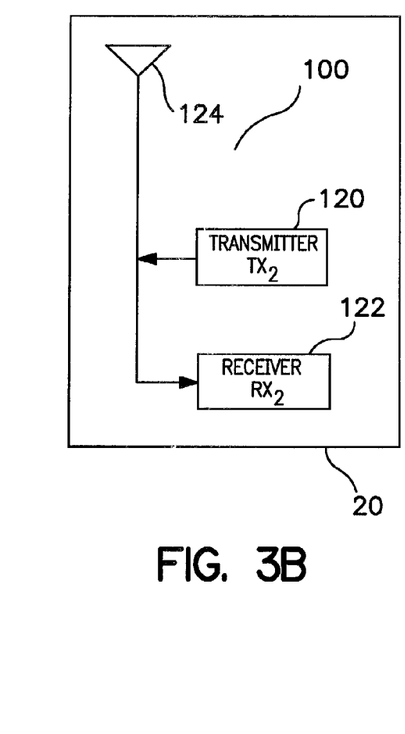
FIG. 3b is a block diagram showing the communication system from the portable extender device of FIG. 1.

Control circuit 112 is responsive to prioritized sets of operational goals to be accomplished in conjunction with each of a plurality of telemetry transmission types, stored in RAM/ROM 42 (FIG. 2). In response to an identification of the type of telemetry to follow, processor 38 (FIG. 2) instructs control circuit 112 as to operational parameters and through control circuitry 112 monitors the outputs of the performance monitoring circuits 106, 108, 110, 111. Under control of processor 38, control circuitry adjusts the various parameter adjustment circuits to achieve the operational goals stored in RAM/ROM 42, in order of their priorities. Control circuitry 112 in some cases adjusts the operational parameters associated with transmitter 104 or receiver 102. Alternatively, parameter adjustment commands may be formatted by processor 38 for transmission by transmitter 104 to receiver 122 (FIG. 3b), to control corresponding parameter adjustment circuits associated with transmitter 120 (FIG. 3b).

In accordance with one aspect of the invention, communication subsystems 44 and portable extender device 20 (FIG. 3a) are preferably capable of exchanging information with each other, such that IMD 10 can transmit, upon command, its stored data related to operational parameters to portable extender device 20. For example, if signal strength detector circuit 108 in subsystem 44 determines that the received signal transmitted from transmitter 120 is unacceptably weak, control circuitry 112 can initiate transmission of a command to subsystem 100 instructing transmitter 120 to increase its transmission power.

In accordance with one aspect of the present invention, the performance goals of the communication system, and the standards or limits imposed upon operational parameters, may themselves be adjusted on a dynamic basis. In this scenario, it would be desirable to increase the minimum transmission range to be maintained by the communication system, so that portable extender device 20 can establish telemetric communication with the patient's implanted device from a longer-than-normal distance, e.g., from bedside or even across the room.

Typically a telemetry system employing the present invention will include a plurality of performance goals applicable in conjunction with each of a variety of telemetry transmission types. In most cases it is envisioned that the performance goals will include one or more absolute requirements for a transmission to be considered acceptable. For example, in most cases a maximum error rate will be the highest priority performance goal, with acceptable error rates differing based on the telemetry type. For example, in the case of downlink of a command to transmit from portable extender device 20 to implanted device 10, the acceptable error rate would typically be lower than for an uplink of stored electrogram data from implanted device 10 to portable extender device 20. Similarly, the performance goal of second priority may differ between two such telemetry transmission types.

The above disclosure assumes that, during initiation of the telemetry link, initial communication between the devices may occur using a telemetry transmission protocol determined to be acceptable for transmission of control signals between the devices, as verified by return transmissions, and that this initial communication will establish the type of telemetry transmission to follow. This protocol may also be used in conjunction with adjustments of the performance parameters, as discussed above. However in many cases, feedback from the receiver to the transmitter is not required to indicate failure of the telemetry protocol in effect to meet the performance parameters. In the case of a transmitted electrogram, implanted device 10 may simply decrease the transmission rate until the minimum transmission rate is reached and thereafter increase power until either a specified maximum power level is reached or until a return transmission from portable extender device 20 indicates an acceptable error rate.

One of the many classes of RF transmission systems for which the present invention is believed to be particularly adaptable is referred to as impulse radio, a technology based upon the pulse position modulation of very low duty-cycle, ultra-wide-bandwidth RF pulses. Impulse radio (OR) pulses are processed with data encoding and pseudo-random noise encoding to smooth the energy in the frequency domain and provide channelization.

FIG. 3b is a simplified block diagram of communication subsystem 100 associated with portable extender device 20. Communication subsystem 100 is preferably compatible with communication subsystem 44 in implanted device 10 and as described herein in the above referenced Goedeke '139 patent. For simplicity in FIG. 3b, however, only transmitter 120, receiver 122 and antenna 124 from communication subsystem 100 are represented in FIG. 3b.

Referring to FIG. 4, portable extender device 20 is a small, easily carried device consisting of several elements that a nurse may use during a home health care visit. For ease and portability, extender device 20 may be equipped with handle 50. Digital pen 52 is used to enter data by touching pen 52 to screen 54. Software to ease the task of entering data will be available in the final form of the present invention. Such software, for example, might have icons to activate downloading of IMD data, FDA forms, prescription forms, and audiovisual elements, among others.

Upon activation, the visiting nurse may use microphone 56 that is the visible portion of an internal cell phone (antenna 60 shown) that is integrated into the portable extender device 20. Available software may be used to provide a list of phone numbers that the nurse may use to contact physicians, other medical experts, druggists, and her next patient, among others. In a similar fashion, small video cam lens 58 is the visible portion of an internal video cam (not shown) that is integrated into portable extender device 20. Video signals of the nurse, or alternatively, of some portion of the patient's anatomy, may be transmitted to a remote expert station (not shown) to facilitate discussion with medical experts available at that station. Additionally, screen captures of various data sets, such as an ECG, may be transferred transtelephonically, or by telemetry, or streaming video. In addition, if the screen capture is deemed necessary for documentation purposes, the image(s) may be automatically converted to HTML or PDF format for transmission and/or storage on a storage disk integrated into portable extender device 20. Since these components are conventional in their design and operation, such components will not be described herein in detail, as it is believed that design and implementation of such components would be a matter of routine to those of ordinary skill in the art.

Figure 5:
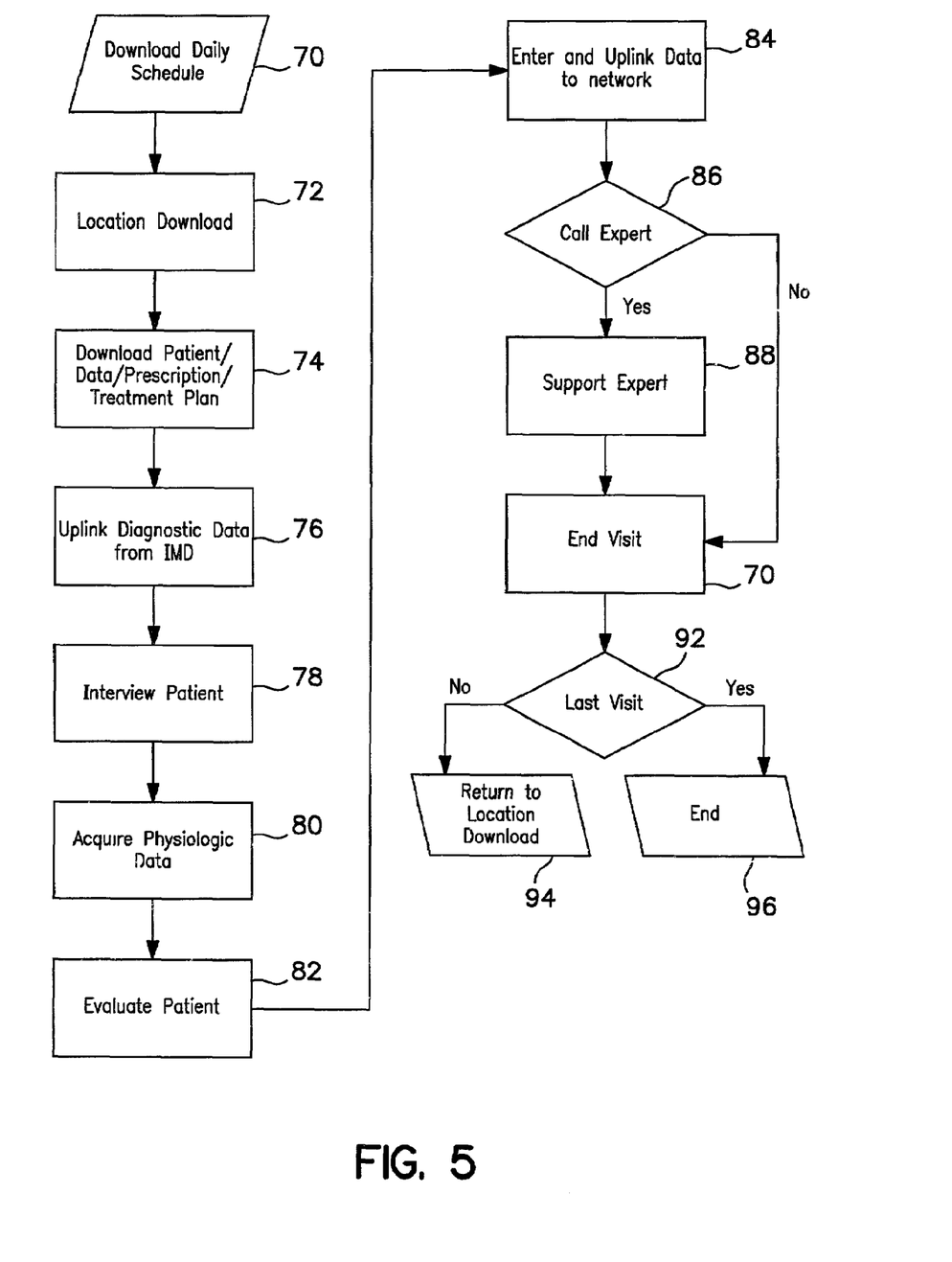
FIG. 5 is a flow diagram of the steps that a visiting health care nurse might follow with the use and help of the portable extender device.

FIG. 5 charts the work flow that a visiting nurse or a health care worker might follow during a normal workday. Before leaving home for her first visit, the nurse would download daily schedule 70 via IrDA, RF cellular, or satellite link from the service or clinic for which she works. Using location download 72, the nurse could use the imbedded GPS system (not shown) to plot the most economical sequence for her visits scheduled for the particular day. At this time, the visiting nurse would gather her equipment, portable extender device, and other materials for her drive to her first patient. The GPS system would give her directions to her patient's home, if she was not familiar with the location.

Upon arriving at the patient's home and a general conversation about the patient's well being, the nurse will activate an icon on portable extender device 20 (FIG. 3) to download patient data 74. In addition, the nurse will activate separate icons to download the patient's prescription and treatment plans 74. Since much of these data are private, the video cam may be used to identify and verify the nurse's identity and her clearance to access secured data. Alternatively, other biometrics may be used for confidential data access, such as fingerprint, voice recognition, iris, or facial recognition. With the prescription plan displayed, the nurse can physically check the prescription containers, their contents, and the number of capsules remaining, along with the expiration date of the prescription. In this way, the nurse will be able to determine any action she might have to take such as, for example, contacting a physician and/or druggist to either refill or renew the prescription. With the treatment plan displayed on screen 58 of portable extender device 20 (FIG. 2), she activates an icon to uplink diagnostic data from IMD 76. Such data might include an ECG tracing, diagnostic data, current IMD setting, chronic pressure or oxygen signal levels from a heart failure monitor such as the Medtronic® Chronicle™, among others. The heart failure monitor may be as described in U.S. patent application Ser. No. 09/809,915 "Heart Failure Quick Look Summary for Patient Management Systems" filed Mar. 16, 2001 and incorporated herein by reference in its entirety. With these data in hand, the nurse interviews patient 78, to determine if/when the patient has experienced any untoward symptoms or complaints related to IMD operation. These complaints, if present, can then be matched against time-stamped diagnostic data to assist further in any diagnostic findings.

Interviewing the patient 78, on the other hand, might bring to light symptoms that are not related to IMD operation. In such cases, the visiting nurse can turn her attention to acquiring physiologic data 80, such as blood pressure measurements, eye examination, skin irritation, among others. With all data in hand, the visiting nurse will form a complete evaluation of the patient 82, along with any questions she may wish to discuss with a physician or other medical expert.

At this juncture, the visiting nurse may wish to contact an expert 86. But, before calling this physician or expert, she must uplink any data to the network 84. These data must be simultaneously available to the physician or other expert at the remote location to facilitate discussion about the patient status and diagnosis. The support expert 88 will advise the nurse of any further steps to be taken. For example, the nurse may have determined that a prescription may need to be renewed. The physician expert 88 can write the prescription and send it directly to the druggist. On the other hand, the expert to be contacted 88 might be the druggist. The nurse could request refills of various prescriptions.

If there is no need to contact a remote expert 86, the visiting nurse might activate a forms icon to fill out any documentation required for reimbursement or any other need. Upon completion of any forms or notes, she would end visit 90. After consulting her daily schedule, the nurse would determine whether this was her last visit 92. If so, this would mark the end of her workday 96. If not, she would activate the location download 72 that would give her directions to her next patient. Upon arriving at her next visit, she would follow the same workflow routine as discussed hereinabove.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed:

1. A portable extender adapted for use by a visiting nurse, the extender comprising:
    a video camera;
    means for establishing a wireless data communication with a medical device implanted in a patient being visiting by the nurse;
    means for downloading diagnostic data from the medical device;
    means for establishing a wireless data communication with a remote location;
    means for downloading secure data corresponding to a treatment and prescription plan for the patient from the remote location;
    means for planning and organizing a daily schedule of patient visits for the visiting nurse; and
    a touch screen coupled to and providing means for a user to activate the video camera, the means for establishing the wireless data communication with the medical device, the means for establishing a wireless data communication with the remote location, the means for downloading the diagnostic data, the means for downloading the secure data, and the means for planning and organizing a daily schedule of patient visits for the visiting nurse.

2. The extender of claim 1 wherein the extender further comprises a means for transferring video images collected by the video camera to a remote location.

3. The portable extender of claim 1, further comprising a GPS system.

4. The portable extender of claim 1, further comprising means to transfer the diagnostic data to the remote location.

5. The extender of claim 1, further comprising a cell phone including a microphone.

6. The extender of claim 1, further comprising a data storage disk.

7. The extender of claim 1, further comprising means for providing identifying information, via the extender, in order to gain access to the secure data.

8. A portable extender adapted for use by a visiting nurse, the extender comprising:
- means for establishing a wireless data communication with a remote location;
- means for downloading a patient visit schedule from the remote location;
- a video camera for verifying the identity of the visiting nurse;
- means for downloading secure data corresponding to a patient treatment and prescription plan from the remote location in response to verifying the identity of the visiting nurse;
- means for displaying the patient treatment and prescription plan;
- means for establishing a wireless data communication with a medical device implanted in a patient being visited by the nurse;
- means for downloading diagnostic data from the medical device; and
- a touch screen coupled to and providing means for the nurse to activate the means for establishing the wireless data communication with the remote location, the video camera, the means for downloading the secure data, the means for establishing the wireless data communication with the medical device, and the means for downloading the diagnostic data.

9. A method implemented in a portable extender, comprising:
- establishing a wireless data communication with a remote location in response to a touch screen activation by a user;
- downloading a patient visit schedule from the remote location in response to establishing the wireless data communication;
- verifying the identity of the user using a video camera image acquired by the portable extender;
- downloading secure data corresponding to a patient treatment and prescription plan from the remote location in response to verifying the identity;
- displaying the patient treatment and prescription plan;
- establishing a wireless data communication with a medical device implanted in a patient in response to a touch screen activation by the user; and
- downloading diagnostic data from the medical device in response to establishing the wireless data communication.

* * * * *